United States Patent [19]

Desforges et al.

[11] Patent Number: 5,252,136
[45] Date of Patent: Oct. 12, 1993

[54] SUGAR COMPOSITION COMPRISING SOLUBLE FIBRE

[75] Inventors: Malcolm Desforges, Near Stamford; Julian M. Cooper, Dereham; Edward L. Williams, Norwich, all of Great Britain

[73] Assignee: British Sugar PLC, Peterborough, Great Britain

[21] Appl. No.: 768,646

[22] PCT Filed: Mar. 29, 1990

[86] PCT No.: PCT/GB90/00466
§ 371 Date: Nov. 18, 1991
§ 102(e) Date: Nov. 18, 1991

[87] PCT Pub. No.: WO90/12117
PCT Pub. Date: Oct. 18, 1990

[30] Foreign Application Priority Data

Mar. 31, 1989 [GB] United Kingdom ............... 8907313

[51] Int. Cl.$^5$ ............... C13F 3/00; A23G 3/00; A01N 65/00; A61K 31/70
[52] U.S. Cl. ............... 127/29; 127/43; 127/30; 426/96; 426/103; 426/804; 426/658; 514/23; 424/195.1
[58] Field of Search ............... 127/29, 43, 30; 426/658, 102, 89, 548, 804, 96, 103; 514/23; 424/195.1

[56] References Cited

U.S. PATENT DOCUMENTS

| | | | |
|---|---|---|---|
| 2,426,076 | 8/1947 | Zenzes | 426/103 |
| 2,801,940 | 8/1957 | Stark et al. | 127/44 |
| 2,807,560 | 9/1957 | Brownell et al. | 127/43 |
| 2,868,646 | 1/1959 | Schapiro | 426/103 |
| 3,305,447 | 2/1967 | Reimers et al. | 167/82 |
| 5,112,638 | 5/1992 | Cagley et al. | 426/460 |
| 5,137,744 | 8/1992 | Cagley et al. | 127/43 |

FOREIGN PATENT DOCUMENTS 035643 9/1981 European Pat. Off.

OTHER PUBLICATIONS

Dietary Fiber, *Food Technology*, Institute of Food Technologist, pp. 35–39, Jan. 1979.
"Technologie des Zuckers", 1955, D. Becker et al., Verlag M. & H. Schaper—pp. 34–37 & 132–133.

*Primary Examiner*—Theodore Worris
*Assistant Examiner*—P. L. Hailey
*Attorney, Agent, or Firm*—Frost & Jacobs

[57] ABSTRACT

A sugar composition consisting of from 90 to 99% by weight sugar and from 10 to 1% by weight of a non-gelling water-soluble dietary fibre. The sugar composition has substantially the properties of normal sugar, but contains a significant amount of dietary fibre, with consequent health benefits. A novel type of soluble fibre derived from sugar beet and a method for preparing it are disclosed. The composition may take the form of a concentrate or syrup, or may be in particulate form. The particulate form may be used as a direct sugar substitute. The fibre used may be a novel fibre obtainable by treating sugar beet with water free from chemical reagents at ambient pressure and at an elevated temperature, for example from 95°–98° C.

29 Claims, No Drawings

SUGAR COMPOSITION COMPRISING SOLUBLE FIBRE

This invention relates to a unique sugar composition containing soluble fibre. The sugar composition has substantially the properties of normal sugar, but advantageously contains a significant amount of dietary fibre, with consequent health benefits. The invention also provides a novel type of soluble fibre derived from sugar beet and a method for preparing it.

Recently, an increase in dietary fibre intake has been recommended for the U.K. population. Over recent years, the proportion of soluble fibre has decreased in the population diet, whilst the insoluble fibre proportion has increased.

Various suggestions have been made to introduce dietary fibre into the diet of humans, but none has found widespread acceptance.

Soluble fibre in the diet is most usually supplemented by means of oat bran or of breakfast cereals enriched with oat bran. Many people find such bran-enriched products distasteful and a majority of the population cannot be expected to consume such bran-enriched diets over the long term.

Sugar compositions containing soluble dietary fibre generally are known. The water-soluble fibre pectin is commonly used as a gelling agent by the food industry, e.g. in jam production. The pectin used in jam production is normally apple or citrus pectin or the naturally occurring pectin in the fruit. The applicant herein markets a jam sugar made by coating damp granulated sugar with a premix containing apple pectin, citric acid and icing sugar in equal quantities by weight. The end product contains 0.67% pectin by weight. A jam sugar containing citrus pectin is also known. Generally, jam sugars contain less than about 1% by weight pectin. The purpose of a jam sugar is to impart sweetness to a jam and more importantly to cause the jam to set or gel. Compositions containing fibre useful as a gelling agent (e.g. apple or citrus pectin) cannot be used in beverages or cooking as a sugar substitute.

One source of fibre is the sugar beet. The principal use of sugar beet fibre is currently in animal feedstuffs. The crude pulp is very distasteful to people and therefore cannot be used as human food. Of the purified, soluble beet fibres, beet pectin has probably attracted most attention. Beet pectin is designated a "pectin" because it contains galacturonic acid, but it has acetate ester groups attached to the polygalacturonic acid and for this reason it does not gel, or at least not in a manner satisfactory to the food industry. As a food product, therefore, beet pectin has not yet found any substantial application.

Commercial preparations of dietary fibre from sugar beet pulp are known. The product sold as Fibrex TM by a subsidiary of the Swedish Sugar Company is an example of such a preparation. Another example is the product sold as Duofiber" by the American Crystal Sugar Company. These preparations suffer the limited acceptance of pure fibre products and have low palatability. The present applicant sells a whole beet fibre product as Beta-Fibre TM, which has been successful in the health food market.

Araban is one example of a fraction of the "soluble fibre" from sugar beet. The extraction process described involves treating a slurry of beet pulp at elevated temperature with calcium oxide.

Water-soluble beet fibre is also found in beet molasses, the liquor remaining after sugar has been extracted from sugar beet. Beet molasses contains sugar, soluble fibre and a miscellany of other by-products of sugar extraction, for example nitrogen compounds. Two thirds of the solids consist of sugar and, because soluble polysaccharide is adhesive, readily clogging the extraction equipment, the soluble polysaccharide content is deliberately kept to a minimum (usually less than 1% by weight although levels as high as 1.56% have been reported). Beet molasses is suitable for feeding to livestock, but is unpalatable to humans.

We have now also discovered in experiments with rats that soluble sugar beet fibre has cholesterol lowering properties, i.e. has a hypocholestrolaemic effect. Soluble fibres also have a beneficial effect on blood glucose and mineral availability.

The object of the present invention is to provide a sugar composition having substantially the appearance and taste of ordinary sugar, whilst providing a significant source of soluble dietary fibre. The intention of the present invention is that the sugar composition of the present invention can be used as a direct replacement for sugar, in any form. It may be, for example, sold in retail outlets alongside normal sugar products or used, in bulk, by the food industry.

Our experiments have shown that, not only does the sugar composition of the present invention increase the level of dietary fibre intake without a noticeable taste or texture, but additionally that an advantageous lowering of cholesterol arises through use of the fibre employed in the composition of the invention.

Since the fibre is water-soluble and significant quantities of insoluble fibre are not present, the dry compositions may be dissolved without the formation of an insoluble residue. This is important not only in the preparation of syrups but also in other applications, for example in the use of the compositions as a beverage sweetener.

The sugar composition essentially contains only natural products, therefore meeting the growing demand for natural, additive-free foods.

According to a first aspect of the present invention, there is provided a sugar composition consisting of from 90 to 99% by weight sugar and from 10 to 1% by weight of a non-gelling water-soluble dietary fibre.

Preferably, the sugar is sucrose, but may be mixture of sugars.

The dietary fibre may be a soluble polysaccharide or a mixture of soluble polysaccharides derived from sugar beet or other fibre which gels too poorly for use as a gelling agent (for example gum arabic or viscosity reduced guar), or a mixture of such fibres.

As used herein, the term "non-gelling" used in relation to a fibre connotes a fibre which gels too poorly for use as a traditional gelling agent to set foodstuffs. Traditional gelling agents include such substances as citrus or apple pectins and lower ester pectins. A "non-gelling" fibre of the present invention may increase viscosity to some extent, but does not produce a gel under conditions associated with traditional gelling agents. It will be understood that a principal object of the invention is to provide a sugar composition having substantially the appearance and taste of sugar and excessive increases in viscosity or actual gelling are not acceptable.

Preferably, the water-soluble fibre is a non-gelling sugar beet water-soluble fibre. The fibre may however be derived from other varieties of the species Beta vulgaris, for example fodder beet, as well as from other plants.

Plant fibre generally contains a mixture of polysaccharides, such as cellulose, pectins and hemicelluloses. It is these polysaccharides which constitute the main components of dietary fibre. Some readily digestible polysaccharides, for example, starch are not considered to be dietary fibre.

Fibre amounts referred to herein in relation to the invention are as determined by the Englyst method (which does not measure ester groups attached to the polysaccharide).

The Englyst method of analysis distinguishes between the different components of dietary fibre. What is normally meant by the term "soluble dietary fibre" is fibre soluble in the gut. Such "soluble fibre" may be either soluble or insoluble in water. The present invention is concerned with fibre which is readily soluble (for example capable of forming a solution, in water, at 20–40% w/w or more, at room temperature e.g. about 20° C.) in water as well as in the gut. For the purposes of the present specification, cellulose and lignin are embraced by the term "insoluble fibre" and non-cellulosic polysaccharides are embraced by the term "soluble fibre". The fibre may comprise a mixture of different types of fibre for example, a mixture may be used of different extracts from sugar beet.

The non-gelling water-soluble sugar beet fibre may be obtained by a process comprising extracting the fibre from beet pulp with water at a temperature above 70° C. and most preferably from 90°, preferably 95°, to 100° C. or to the boiling point of the mixture, e.g. 95°–100° C.

The non-gelling water-soluble fibre from sugar beet can be extracted from two sources, namely the washed and sliced sugar beet itself or, more typically, from the residual vegetable material (sugar beet pulp) after the extraction of sugar. If sugar beet is used as the feedstock, it may be necessary to blanch the material before extraction of water-soluble fibre and sugar. The exhausted pulp obtained after conventional extraction of sugar may be pressed to obtain the maximum yield of sugar, then dried. However, any of the wet pulp before pressing or pressed pulp after pressing or the dried pulp can also be used as feedstocks for water-soluble fibre extraction.

The feedstock is extracted with an aqueous medium, such as water at a temperature above 70° C., more preferably above 90° C., and most preferably in the range from 95°–100° C. Above 100° C. a pressurised system is required, typically pressures of from 1 to 5 bar are used. If temperatures above 100° C. are used, the maximum temperature is about 135° C.

All or part of the "soluble fibre" from sugar beet or pulp can be extracted and made water-soluble using extraction media with pH values in a very broad range (pH 1 to 12). The preferred pH for the extraction medium is from pH 4 to 9 and more preferably from pH 5 to 7. Most preferably, the extraction medium is water at approximately neutral pH without the addition of acid or alkali or of other reagents.

The extraction may be carried out for from 5 to 120 minutes, preferably from 15 to 60 minutes and most preferably from 20 to 30 minutes, as sufficient for extraction.

Water, optionally containing any chemical agents, is added to the feedstock (beet or pulp) to produce a mobile slurry. The ratio of water to feedstock can typically be from 1:1 to 10:1 (w/w) for beet and from 1:1 to 10:1 (w/w) for pulp. Ideally, ratios are 5:1 (w/w) for beet, 5:1 (w/w) for pressed pulp and 2:1 (w/w) for wet pulp. The water may be fresh water or water condensate from a stage in the process.

The slurry is stirred throughout the reaction in a tank or mixer, or in a series of continuously stirred tank reactors, or in a concurrent or counter-current extractor. Following extraction, the dissolved water-soluble fibre is separated from the insoluble residue using processes such as decantation and pressing. The solid residue can be washed at this stage to increase the yield of dissolved fibre.

Extractions can produce a range Of mixtures of sugar and water-soluble fibre depending on the feedstock and extraction conditions. The composition of the fibre depends on the extraction conditions such as temperature and pH, and the range of the proportions of neutral sugars to uronic acids may be 1:10 to 10:1 (w/w), typically 10:90 to 40:60 (w/w). Extractions from sugar beet yield mixtures in the range 97:3 to 75:25 (w/w) sugar:-soluble fibres; from wet pulp 80:20 to 40:60 (w/w); and from pressed pulp 50:50 to 2:98 (w/w).

The soluble fibre is polydisperse with a peak molecular weight of around 100,000 to 200,000. The uronic acid is present as poly D-galacturonic acid, partially esterified with methyl groups at $C_6$ and acetyl groups at $C_2$ or $C_3$. The neutral sugars are typically about 80% L-arabinose, 15–19% D-galactose and 1–5% L-rhamnose (in each case percentages are expressed as weight percentages of neutral sugars).

The dilute solution of water-soluble fibre and sugar is filtered or centrifuged to remove pulp debris. The fibre solution may optionally be purified, for example to remove part or all of the taste, odour or colour, by passage through absorbent materials such as carbons or ion exchange resins. As the resin, there may be used one or more of those sold under the designation Amberlite XAD (Trade Mark) by Rohm and Haas. The taste and odour without this step are quite different from the characteristic unpleasant taste of sugar beet. The solution is concentrated using conventional techniques such as evaporation or membrane separation.

It may be desirable for the concentration step to comprise ultrafiltration to remove any undesirable odour. For example, the concentration could be conducted using ultrafiltration as the first stage, followed by evaporation, for example. If the solution has not been purified, the fibre normally has an acceptable (caramel) odour but purification may leave an unacceptable odour.

At this stage, it is also possible to separate the water-soluble fibre from sugar present in the extracted liquor. The separation may be performed by ultrafiltration or by precipitating the fibre with an organic solvent such as isopropyl alcohol, for example. The fibre can then be used as a hydrocolloid similar to araban as described in the Applicant's copending International patent application PCT/GB89/01452, with uses included but not restricted to those described for araban.

The mixtures of water-soluble fibre and sugar can be further processed by several routes to yield a product containing sugar and soluble fibre in the required ratio.

The concentrate of sugar and water-soluble fibre can be dried using equipment known to those skilled in the art, for example spray drying, roller drying and drum drying. These processes will yield dried materials such as crystals, powders or films. More typically, however, it is necessary to add sugar to obtain the desired ratio.

This can be achieved in several different ways to give products differing in appearance and uses.

The water-soluble fibre and sugar can be combined in the desired ratio by dry mixing. They may be bound together using water and subsequent drying.

The desired ratio of soluble fibre to sugar can also be achieved by coating sugar with the concentrate of water-soluble fibre and drying. The desired ratios can also be achieved by mixing a solution of sugar with a solution of water-soluble fibre and drying or concentrating to a syrup.

Sugar can also be added to the concentrate to give the desired ratio and the composition isolated using a suitable technique, for example direct drying (spray drying, drum drying, roller drying) or co-crystallisation.

The concentrate can also be used as an ingredient in food formulations without the need to isolate a solid dry product.

The dried fibre extract may be stored prior to use, e.g. as granules or as a powder. If stored as granulest these would be ground to a powder before formulating the desired preparation.

The preferred method of extraction the fibre uses pressed sugar beet pulp after extraction of the sugar as the feedstock and pressing. The preferred method has the following steps:

1. Wash pulp, if necessary
2. Extract fibre in one or more stirred tanks arranged for counter- or co-current extraction at elevated temperature (preferably greater than 95° C.)
3. Filter or centrifuge the extraction medium and optionally recycle a portion thereof
4. Concentrate the extraction medium (e.g. with a falling film evaporator)
5. Spray dry the concentrate
6. Formulate composition by applying dried material to wetted sugar.

Preferably, extraction step (2) is carried out at ambient pressure. It is further preferred that no chemical agents be used in the extraction step.

Steps (5) and (6) above may be replaced by a single step of coating sugar with concentrate. An appropriate method of coating is spray coating, which simultaneously effects coating and drying.

The extraction step is preferably performed in a co-current process using a series of continually stirred tank reactors. For example, a number of continually stirred tanks are arranged at successively decreasing elevations. Pulp and water enter the top of each top tank and flow to the next succeeding tank down the series.

The fibre is normally associated with minor amounts (e.g. up to 40% by weight of the dried extract) of sugar and other substances extracted from the beet with the fibre.

In general, the sugar compositions may contain minor proportions of other materials which do not destroy the utility of the composition. The fibre should normally be readily soluble, e.g. form solutions of 20–40% (w/w) fibre or more.

The fibre is generally in an amount of from 1 to 10% by weight, preferably 1 to 7.5% by weight, the balance essentially being sugar.

The proportion of fibre in the composition is dictated, at least in part, by the intended use of the composition. We have found that the addition of the fibre to sucrose can have two important effects on the properties of the sugar. These are (1) reduction in perceived sweetness and (2) interference with the cooking properties of sucrose. In order for the composition to be usable as a sugar substitute in substantially all normal applications, the solubility, viscosity, gelling properties and quantity of the fibre should be such that, in normal usage, the perceived properties of the sugar should not be altered.

In the case of sucrose combined with beet fibre, a fibre content of above about 10% (w/w) appears in general to destroy the normal utility of the sugar for many applications. At these high fibre contents, sucrose may be acceptable purely as a sweetener, for example in beverages, but at 10% (w/w) fibre content sucrose is at the limits of acceptability as a beverage sweetener. If much more fibre is combined with sucrose, the reduction in perceived sweetness and the effect of the fibre on the taste and feel of beverages would appear normally to be unacceptable.

At 10% (w/w) fibre content, we have found a sucrose/beet fibre composition to be unsuitable for baking, because products do not rise. A composition containing 7.5% (w/w) fibre has been found acceptable purely as a sweetener but normally unacceptable for baking. At 5% (w/w) fibre, we have found the composition to be acceptable in baking although the product is different. A composition containing 2.5% (w/w) fibre appears to have the same properties as pure sucrose.

As the fibre content diminishes, the value of the composition as a fibre source naturally decreases, and for this reason it is not envisaged that a fibre content of less than 1% would normally be used. In practice a fibre content of between 2.5% or 3% and 5% or 6%, especially of 3–4%, e.g. 3.5%, is to be preferred. We have found that 3% fibre results in an acceptable 20% reduction in perceived sweetness.

The fibre content is therefore from 1 to 10% by weight, preferably from 1 to 7.5% by weight, more preferably from 1 to 5% by weight, more preferably 2.5 to 6% by weight, more preferably 3 to 5% by weight, most preferably about 3% by weight.

Preferably the sugar composition according to the first aspect of the invention is particulate and suitably free-flowing. It resemble granulated sugar (i.e crystalline sugar dried in a granulator) of normal size (mean particle size of about 550 $\mu$m), or castor sugar (mean particle size less than about 400 $\mu$m) or icing sugar (mean particle size less than about 100 $\mu$m). The natural compositions have an attractive golden colour and can also be sold as coffee crystals. Suitable compositions, with an appropriate fibre content, may be sold at retail outlets or to the food industry as a sucrose substitute usable in place of sucrose in all applications. Suitably, the particulate sugar composition has a particle size of greater than 100 $\mu$m.

In a second aspect of the invention, there is provided a sugar product comprising sugar coated with a sugar composition of the first aspect of the invention. Preferably, the overall composition of the sugar product is such that it consists of from 90 to 99% by weight sugar and from 10 to 1% by weight of a non-gelling water-soluble dietary fibre.

In a third aspect of the invention, there is provided a liquid sugar product comprising the sugar composition according to the first aspect of the invention in combination with water. The dry compositions of the invention may be dissolved in water to form a syrup or concentrate, which can be used as an ingredient in food formulations. Alternatively, the syrup may be prepared directly in the manufacturing process, without the prior manufacture of dry composition.

The syrups or concentrates are similar in sugar content to normal liquid sugar/syrup. Generally this is the highest stable solids content. That is, it depends on the solubility of the sugars. This is around 67% w/w for sucrose to over 80% w/w for sucrose/invert sugar mixtures.

Thus, the syrups typically contain from 62-72 wt. % sucrose based on the total weight of sucrose and water, preferably 65-69% sucrose and most usually about 67% sucrose, and are generally referred to as "liquid sugar". The syrups can be used in the preparation of many food products, especially soft drinks. The syrups may contain other ingredients than sucrose and soluble fibre, and in particular additional or alternative sugars may be present. Notably, the solids content of the syrup may be increased by including invert sugar as well as sucrose; in this case a solids content of 75 to 87 wt. % based on the total weight of sucrose, invert sugars and water, and most preferably of up to about 85%, is usual.

The fibre:sugar weight ratio in the syrups is the same as the fibre:sugar weight ratio in the dry compositions of the invention. However in syrups containing a mixture of sucrose and one or more other sugars it may be convenient to prepare the syrup using a solid or liquid sucrose/fibre composition taken from the production process for the dry product, in which case the fibre:sucrose weight ratio, but not necessarily the fibre:total sugar ratio, will correspond to the proportions found in the solid products of the invention.

It will be understood that the sugar products may contain other ingredients common in the food industry, such as colourings or flavourings.

The various novel compositions of the invention may be used in the making of foods and beverages and of preparations for making foods or beverages.

In a fourth aspect of the invention, there is provided a process for making a food, a beverage or a preparation therefor, in which a composition of the first aspect of the invention or a sugar product according to the invention is applied to or combined with other material (e.g. other ingredients or an intermediate preparation or composition) and the resultant preparation is further processed, if necessary, to form the desired product.

The sugar compositions of the invention may be formed into, for example, snacks or breakfast cereals by being used as an ingredient in a cooker extruder. The novel fibre of the invention may be used in like manner.

Although the compositions of the invention consist essentially of sugar and water-soluble fibre, they may also contain minor amounts of other substances which do not have a significantly deleterious effect on the composition. In particular the fibre will often be associated with other components of the plant from which it was extracted. For example, the fibre extracted from sugar beet by the process of the invention contains minor amounts of other beet components (including sugar) extracted with the fibre; these components may impart to the fibre (and to the sugar/fibre composition) a slight odour. Odour can also come from the fibre itself. The odour may be pleasant. The process may be modified as described above to control the odour, if desired.

The composition of the sugar beet extract depends upon the feedstock and the extraction conditions (e.g. time). Typically, in preferred embodiments the fibre content of the dried sugar beet fibre extract, measured by the Englyst method, is 60-80% by weight of the extract, e.g. 65-75%; generally, the sucrose content of the fibre extract is from 10-30% by weight and is usually from 15 to 25%, e.g. in the order of 20%. The remainder of the extract is other sugars (glucose, fructose), ash and possibly other minor constituents.

The total content of glucose and fructose is usually less than 0.1% w/w, but may be as high as 6-7% by weight of the extract or from less than 0.1 to 9-10% by weight of the fibre (all depending on the feedstock and extraction conditions).

The ash content is up to 15%, suitably 5-15%, more typically 12-13%, by weight of the extract or up to 25%, preferably 12.5-25% by weight of the fibre and more usually 15-20% by weight of the fibre (all depending on the feedstock and extraction conditions). Protein and other minor constituents are often present in negligible amounts but protein contents of up to 3% by weight of the extract (4-5% of the fibre) may occur. The ash contains potentially beneficent mineral nutrients. The typical sugar beet fibre ratios attained by extracting different types of starting material are further described below, and indicate the wide variation possible in the extract composition.

Where quantities or proportions of fibre are quoted in this specification, the values given refer to the amount of fibre excluding associated substances.

According to a fifth aspect of the invention, there is provided a non-gelling water-soluble sugar beet fibre obtained by a process comprising extracting the fibre from beet pulp with water at a temperature above 70° C. and most preferably from 90°, preferably 95°, to 100° C. or to the boiling point of the mixture, e.g. 95°-100° C.

The preferred parameters of the process and therefore the definition of the preferred fibre are as mentioned immediately above.

The novel fibre of the invention, whether in purified form or as crude extract, can be used as a dietary fibre supplement, a bulking agent or as a blood cholesterol reducing agent. The fibre can also be used as a hydrocolloid similar to araban as described in the Applicant's copending International patent application PCT/GB89/01452, with uses included but not restricted to those described for araban.

In particular the novel fibre may be included in (non-sugar) sweetener preparations, and compositions of the novel fibre and sweetener constitute a sixth aspect of the invention. The novel fibre may also be formed into a composition for use as a blood cholesterol reducing agent; the composition may take the form of tablets.

The invention further provides, in an seventh aspect, a sugar composition according to the first aspect of the invention for use in reducing blood cholesterol and the use thereof in the manufacture of a medicament for reducing blood cholesterol.

According to a eighth aspect of the invention, there is provided a process for making a non-gelling water-soluble sugar beet fibre comprising extracting the fibre from beet pulp with water at a temperature above 70° C. and most preferably from 90°, preferably 95°, to 100° C. or to the boiling point of the mixture, e.g. 95°-100° C.

The preferred parameters of the process are as mentioned above.

According to a ninth aspect of the invention, there is provided a method of reducing blood cholesterol comprising administering an effective amount of a sugar composition according to the first aspect of the invention.

The invention will now be described in more detail by way of example only.

EXAMPLE 1

The sugar beet pulp used in this example consists of sugar beet cossettes which have been passed through a diffuser to extract sugar and then been pressed in a screw press. It will be referred to hereinafter as "pulp".

500 liters of water at 60° C. were taken in a stainless steel, steam heated, interrupted spiral trough mixer and heated to 90° C. 100 kg of pulp (at 23 weight % dry matter) was added to the mixer. The mixer contents were heated to 95° to 98° C. and kept at this temperature for 1 hour with frequent mixing.

The mixer contents were then transferred to nylon net bags which were pressed in a hydraulic press and the extracted juice (450 liters at pH 6 and 1.3% Refractive Dry Substance (% RDS)) transferred to a stainless steel tank. The pressed extracted pulp (133 kg at 14.6 weight % dry matter) was discarded.

The extracted liquor was passed through a plate and frame filter press. The dilute liquor, i.e. 1.3-1.4% RDS was concentrated to 40% solids, by evaporation under vacuum. Sugar was added to raise the solids content of the liquid to 60 weight %. At this stage, the liquor needs to be heated. 344 g (2×172 g, added in two batches) of this 60% solids syrup was added to 1293 g of sucrose, drying in a granulator between additions. Final product: Total solids 1.5 kg; consisting of 1293 g granulated sugar+344 g syrup containing 113 g soluble fibre (7.5% by weight of solids)+93 g sucrose (including 60 g of sucrose added).

EXAMPLE 2

The 60% solids solution from Example 1 was dried to produce a further composition of the invention.

EXAMPLE 3

An extraction was carried out in a series of four stainless steel stirred tanks each of approximately 60 liters capacity, mounted so that the overflow from one tank cascaded into the next tank in series. The contents of the tanks were heated to 95° C. by steam injection. 144 kg/hour of pressed pulp (23% dry matter) were fed into the top tank of the system using a variable speed screw conveyor. A total of 720 kg/hr of liquor or water were added to the top tank (i.e. a water to pulp ratio of 5:1). A typical make up of this liquor was 145 kg/hr of demineralised water and 575 kg/hr of recycled liquor.

The mixture of pulp and liquor was pumped out of the fourth tank and the majority of the pulp separated by passing through a sack made of plastic mesh. The pulp was pressed on a pilot scale screw press and dried on a pilot scale rotary drier. The liquor was split into two streams, one of which was recycled as described above. The liquor from the press was also recycled. The liquor sent forward had a solids content of 2.5%. It was sent at a rate of 145 kg/hr to a Westphalia Separator (a type of continuous centrifuge) which removed any remaining pulp as a sludge of 10% dry substance and flow rate 1.5 kg/hr.

The liquor was then evaporated from 2.5% solids to 35% solids on a vacuum evaporator made from Corning QVF glass components. The evaporator treated 75 liter batches, operating under vacuum at a temperature of 60°-80° C.

The concentrated liquor was dried in a spray drier (Niro Production Minor) at an inlet temperature of 200° C. and an outlet temperature of 90° C. 10.4 kg/hr of liquor were dried to 4 kg/hr of powder at 92% dry matter.

EXAMPLE 4

Addition of Spray Dried Fibre to Wet Granulated Sugar (5% Fibre Addition)

General Method

1. Granulated sugar was moistened using a fine mist spray of fibre syrup (20 RDS, 2.5% water addition) using a suitable mixer e.g. interrupted spiral or paddle blade mixers.
2. The required quantity of spray dried fibre powder was then added whilst the mixer was still running.
3. The damp fibre/ sugar mixture was then dried using a fluid bed drier or granulator.

SPECIFIC EXAMPLE (for 2 kg batch at 5% fibre: Fibre syrup 58% fibre, 13% sugar—20 RDS)

1. Granulated sugar (1877 g) was weighed into the mixer.
2. Fibre syrup (59 g, 20 RDS) was sprayed to moisten the granulated sugar.
3. Spray dried fibre powder was then added (160 g powder) to give the final 5% fibre inclusion level.
4. The product was then dried using a granulator.

EXAMPLE 5

Fluid Bed Coating of Granulated Sugar with Fibre Syrup

General Method

1. A spouted fluid bed drier was charged with granulated sugar.
2. The bed of sugar was heated to 80° C.
3. Fibre syrup (25 RDS) was sprayed into the preheated bed of sugar. The spray rate was initially slow but was doubled after 15 minutes. The total cycle time was 30 minutes.

SPECIFIC EXAMPLE (for a 10 kg batch at 5% fibre)

1. Fibre syrup 58% fibre, 13% sugar—25 RDS. The spouted fluid bed was charged with 9.05 kg of granulated sugar.
2. The fibre syrup was added at a rate of 80 ml. min$^{-1}$ for 15 minutes then at 150 ml. min$^{-1}$ for 15 minutes. Total fibre syrup addition was 3.45 kg.
3. Air temperature profile was 80° C. inlet temperature and 45° C. outlet temperature.

EXAMPLE 6

The sugar composition of the invention was used as a direct replacement for sugar in recipes with a high sugar content. The sugar composition used in the recipes comprised sugar and about 3% w/w water-soluble sugar beet dietary fibre.

Chocolate Cake 15 ml lemon juice
200 ml milk
125 g margarine
250 g Sugar Composition
150 g egg
225 g plain flour
5 ml baking powder
50 g cocoa powder
Good result—light and moist

Oat Cookies 175 g self raising flour
5 ml baking powder
175 g Sugar Composition
175 g margarine
75 g porridge oats
25 g syrup
Good result—crisp, good flavour

Chocolate Chip Cookies 75 g margarine
175 g Sugar Composition
50 g egg
10 drops vanilla essence
50 g chopped walnuts
175 g self raising flour
2.5 ml bicarbonate of soda
75 g chocolate drops
Fair result—slightly chewy.

American Brownies 50 g plain chocolate
125 g margarine
175 g Sugar Composition
100 g egg
100 g S.R. flour
50 g chopped nuts
Good results.

Caramel Fingers

Shortbread Base 125 g margarine
75 g Sugar Composition 175 g plain flour

Caramel Topping 200 g condensed milk
125 g margarine
125 g Sugar Composition
50 g syrup To make base: place all ingredients in Kenwood mixer and mix until mixture forms a ball. Roll out and press into a shallow tin. Bake at 180° C for 15-20 mins until golden brown.

Filling: place all ingredients in pan. Heat gently until sugar composition of the invention dissolves. Slowly bring mixture to the boil, stirring continuously. Boil for 7 minutes, stirring. Spread over base and allow to cool and set. Can be covered with a layer of chocolate.

Good result.

EXAMPLE 7

Experiments were conducted to investigate the cholesterol-lowering properties of the sugar compositions of the invention.

The method for testing fibres to determine whether they are potent cholesterol-lowering agents is not standardised and a number of techniques including animal and clinical trials have been used.

The approach adopted to test the potential of sugar beet fibre to lower blood cholesterol was devised in association with the Institute of Food Research, Norwich, who have used rat studies to test a number of different fibrous materials. The animal model adopted has successfully demonstrated the cholesterol-lowering potential of fibres known to be active in cholesterol reduction in man.

Sugar beet fibre (Beta Fibre) manufactured by British Sugar plc., has been demonstrated (in unpublished work) to lower blood cholesterol in both animal trials using the above protocol (Johnson et al, British Journal of Nutrition, in press) and in clinical trials with normal subjects (Morgan et al 1989) and diabetic subjects (Travis et al, in press).

The following experiments were carried out to demonstrate the effectiveness of the fibre employed in the sugar composition of the invention.

Method

Groups of animals (male Wistar rats ca 100 g live weight) were used for each of the dietary treatments described. The experiment began by feeding all groups of animals for two weeks with a pretest semi-synthetic diet. During the first four days the diet was fed ad libitum and then for the next ten days at 80% of the previous intake to obtain a level which would be regularly consumed during the trial period.

After the pretest period, one group of animals, group O, were slaughtered as negative control, the other groups continued for the rest of the experimental protocol.

The experimental groups were as follows:

| Group | | |
|---|---|---|
| | 1 | Basal control (Semi-synthetic + cellulose) |
| | 2 | Treatment A (Semi-synthetic + soluble sugar beet fibre) |
| | 9 | Control C (Semi-synthetic high cholesterol + cellulose) |
| | 10 | Treatment CA (Semi-synthetic high cholesterol + soluble sugar beet fibre) |

After the pre-test period animals were randomly ascribed to each group. If necessary animals were re-randomised so that body weights were equalised.

Immediately after randomisation and prior to receiving the test diets the animals were starved and a blood sample taken in the fasted state at the commencement of the study. A further sample was taken after 28 days on the diet when the animals were taken in a fasted state. The animals were then slaughtered.

The required quantity of the diet was calculated to be 15.4 g/day, this enabled all animals to receive 1.26 g non starch polysaccharide as either cellulose (a control fibre known not to reduce cholesterol) or sugar beet fibre (treatment A and CA).

Food intakes were monitored every day of the balance period. Body weights were measured at the beginning and end of each test period and when sampling blood.

Approximately 1 ml blood samples were taken and centrifuged immediately. The serum removed and stored at $-20°$ C. until analysed for cholesterol by commercial assay kit CHOD-PAP, C-system Boehringer, UK.

The results were analysed by using analysis of variance with multiple regression models, least significant differences (LSD) were calculated using the unexplained variance.

The coefficients $C_1$, $C_2$, $C_9$, $C_{10}$ are the separate group dietary mean values for the change in serum cholesterol and is the unaccounted variance used to calculate the LSD. Table 1 shows the results from the experiment.

TABLE 1

The change in serum cholesterol in the unfed state of rats fed control or soluble sugar beet fibre diets

| | Diet | | Change in cholesterol (Day 28-1) | LSD |
|---|---|---|---|---|
| Group | 1 Control | $C_1$ | $-0.1464^b$ | 0.4203 |
| | 2 Treatment A | $C_2$ | $-0.4729^{ab}$ | |
| | 9 Control C | $C_9$ | $0.6860^b$ | 0.4203 |
| | 10 Control CA | $C_{10}$ | $0.0773^a$ | |

Means values with different superscripts letters are significantly different ($P>0.05$).

From these results it can be seen that the cholesterol level was markedly lower in both treatment groups A+CA compared to their respective controls. In the case of the control c this difference was statistically significant at the 5% level. In the basal control the difference just failed to reach statistical significance.

This experiment demonstrates that soluble sugar beet fibre prepared by the method described in this specification when incorporated into the diet of rats at moderate levels (ca 8%) like its parent (whole sugar beet fibre) lowers serum cholesterol by a significant amount.

The animal model used for this study is similar to that described by Johnson et al 1990, in their work on Beta Fibre and so it can be anticipated that when soluble sugar beet fibre is fed in clinical studies it too will lead to significant lowering of serum cholesterol.

It will be understood that the invention is described above by way of example only and that modifications of detail may be made within the scope of the invention.

We claim:

1. A solid, particulate, sugar composition comprising crystalline sugar coated with a non-gelling water-soluble dietary fibre, the sugar composition comprising from about 90 to 99% by weight sugar and from about 10 to 1% by weight of non-gelling water-soluble dietary fibre.

2. A sugar composition according to claim 1 wherein at least a portion of the non-gelling water-soluble dietary fibre is sugar beet fibre.

3. A sugar composition according to claim 2 wherein the sugar beet fibre is obtained by a process comprising the step of extracting the fibre from beet pulp with water at a temperature above about 70° C.

4. A sugar composition according to claim 3 wherein the extraction is carried out at from about 95° to 100° C.

5. A sugar composition according to claim 2, which additionally contains ash in an amount of up to about 25% by weight of the fibre, and glucose and fructose in a total amount of up to about 10% by weight of the fibre.

6. A liquid sugar product comprising the sugar composition according to claim 2, in combination with water.

7. A liquid sugar product as claimed in claim 6 wherein said sugar comprises sucrose, and further wherein said sucrose is present in an amount equal to approximately 62 to 72 wt % of the total weight of sucrose and water in said product.

8. A liquid sugar product as claimed in claim 6 wherein said sugar comprises sucrose and invert sugar, and further wherein said sucrose and invert sugar are present in an amount equal to approximately 75 to 87 wt % of the total amount of sucrose, invert sugar and water in said product.

9. A sugar composition according to claim 2, wherein the fibre content is about 3% by weight.

10. A sugar composition according to claim 1, wherein the fibre content is about 3% by weight.

11. A sugar composition according to claim 1, which additionally contains ash in an amount of up to about 25% by weight of the fibre, and glucose and fructose in a total amount of up to about 10% by weight of the fibre.

12. A liquid sugar product comprising the sugar composition according to claim 1, in combination with water.

13. A medicament for reducing blood cholesterol comprising the sugar composition according to claim 1 or 2.

14. A sugar composition comprising from about 90 to 99% by weight sugar and from about 10 to 1% by weight of a non-gelling water-soluble dietary fibre wherein at least a portion of the non-gelling water-soluble dietary fibre is sugar beet fibre.

15. A sugar composition according to claim 14 wherein the sugar beet fibre is obtained by a process comprising the step of extracting the fibre from beet pulp with water at a temperature above about 70° C.

16. A sugar composition according to claim 15 wherein the extraction is carried out at from about 95° to 100° C.

17. A sugar composition according to claim 14, which additionally contains ash in an amount of up to about 25% by weight of the fibre, and glucose and fructose in a total amount of up to about 10% by weight of the fibre.

18. A liquid sugar product comprising the sugar composition according to claim 14, in combination with water.

19. A liquid sugar product as claimed in claim 18 wherein said sugar comprises sucrose, and further wherein said sucrose is present in an amount equal to approximately 62 to 72 wt % of the total weight of sucrose and water in said product.

20. A liquid sugar product as claimed in claim 18 wherein said sugar comprises sucrose and invert sugar, and further wherein said sucrose and invert sugar are present in an amount equal to approximately 75 to 87 wt % of the total amount of sucrose, invert sugar and water in said product.

21. A food comprising the sugar composition of claim 14.

22. A beverage comprising the sugar composition of claim 14.

23. A sugar composition according to claim 14, wherein the fibre content is about 3% by weight.

24. A medicament for reducing blood cholesterol comprising the sugar composition according to claim 14.

25. A liquid sugar product as claimed in claim 12 wherein said sugar comprises sucrose, and further wherein said sucrose is present in an amount equal to approximately 62 to 72 wt % of the total weight of sucrose and water in said product.

26. A non-gelling water-soluble sugar beet fibre obtained by a process comprising extracting the fibre from beet pulp with water at a temperature above 70° C.

27. A sweetener composition comprising a sweetener and a water-soluble dietary fibre according to claim 26.

28. A medicament for reducing blood cholesterol comprising the non-gelling water-soluble sugar beet fibre according to claim 26.

29. A process for making a non-gelling water-soluble sugar beet fibre comprising extracting the fibre from beet pulp with water at a temperature above 70° C.

* * * * *